United States Patent [19]

Ishibashi

[11] Patent Number: 5,200,052
[45] Date of Patent: Apr. 6, 1993

[54] ION CONCENTRATION ANALYZER

[75] Inventor: Kiyochika Ishibashi, Tokyo, Japan

[73] Assignee: Olympus Optical Co., Ltd., Tokyo, Japan

[21] Appl. No.: 802,872

[22] Filed: Dec. 6, 1991

[30] Foreign Application Priority Data

Dec. 25, 1990 [JP] Japan .................. 2-405998

[51] Int. Cl.⁵ ............................................ G01N 27/26
[52] U.S. Cl. .................................... 204/409; 204/416
[58] Field of Search ............... 204/400, 409, 416, 422, 204/435, 405

[56] References Cited

U.S. PATENT DOCUMENTS 4,343,767 8/1982 Long et al. .................... 204/409
4,604,166 8/1986 Weinberg et al. ............. 204/400
5,102,526 4/1992 Brown et al. .................. 204/418

FOREIGN PATENT DOCUMENTS 60-143756 7/1985 Japan.

Primary Examiner—John Niebling
Assistant Examiner—Bruce F. Bell
Attorney, Agent, or Firm—Frishauf, Holtz, Goodman & Woodward

[57] ABSTRACT

An ion concentration analyzer for determining ion concentration in blood or urine. This analyzer comprises a flow cell provided with an ion selecting electrode and a syringe having a metal piston rod for introducing sample liquid into the flow cell. A metal member is disposed at a mid portion of a pipe connecting the flow cell and the syringe, and is electrically connected to the piston rod.

4 Claims, 3 Drawing Sheets

ION CONCENTRATION ANALYZER

BACKGROUND OF THE INVENTION

1. Field of the Invention

The present invention relates to an ion concentration analyzer of the flow cell type which uses an ion selecting electrode to determine ion concentration in blood and urine. 2. Description of the Related Art The ion concentration analyzer usually uses a rolling pump or a syringe pump as means for introducing sample liquid into the flow cell. It is more preferable to use the syringe pump in the case where the amount of sample liquid introduced is not changed by aging and an assay of high accuracy is required.

The conventional syringe, usually used for this syringe pump, has the structure shown in FIG. 3. A sliding block made of elastic resinous or rubber insulating material suited for sealing such as polytetrafluoroethylene (hereinafter referred to as PTFE) is fixed to the distal end of a metal piston rod 3, which is slidably inserted into a glass or plastic cylinder 1. This syringe thus arranged is often used in automatic analyzers, because it can introduce a predetermined amount of liquid with high accuracy and efficiency, and also because it is highly durable.

When the sliding block 2 is worn out, however, the liquid leaks from the syringe at the portion worn out, and will contact the metal piston rod 3. Consequently, voltage noise is generated while the syringe is operated.

The ion concentration analyzer, which has an ion selecting electrode to measure a low voltage, must be provided with means for preventing any influence of the voltage noise on the ion selecting voltage.

As disclosed in Published Unexamined Japanese Patent Application No. 60-143756, one of the conventional methods of avoiding the voltage noise is to connect an a ground to a portion adjacent to an electrode for measuring an electric voltage so as to discharge the voltage noise out of the ion concentration analyzer.

The ion concentration analyzer of a flow cell type, in which this noise-preventing measure is taken, is shown in FIG. 3. The ion concentration analyzer comprises a flow cell 6, a sucking nozzle 5, and a syringe 12. The flow cell 6 has openings through which sample liquid will be fed and discharged. The a sucking nozzle 5 is connected to one of the openings of the flow cell 6. The syringe 12 is connected to another opening of the flow cell 6 by a metal pipe 9 and a check valve 11a.

More specifically, an ion selecting electrode 7 and a reference electrode 8 are attached, at one end, to the flow cell 6 and, at the other end, to an arithmetic unit 15. The arithmetic unit 15 calculates the ion concentration of sample liquid. Further, the sample sucking nozzle 5 is connected to a nozzle drive system 4 and can be appropriately lowered to a sample 13 transferred below the nozzle 5 to suck the sample 13.

As has been described with reference to FIG. 3, the syringe 12 comprises the glass cylinder 1 and a piston slidably inserted in the cylinder 1. The piston has the sliding block 2 which is made of elastic insulating matter such as polytetrafluoroethylene and secured to the distal end of the metal piston rod 3. The piston rod 3 has a flange at the proximal end. The flange is connected to a syringe drive mechanism 16. Hence, the mechanism 16 can drives the piston rod 3 back and forth in the glass cylinder 1.

A pipe line 17 is connected, at one end, to the syringe 12 and to an outlet port, at the other end. A check valve 11b is provided on the pipe line 17.

The metal pipe 9 arranged on the liquid flow path is connected to a ground, thereby grounding the sample liquid flowing through the pipe line connecting the flow cell 6 to the syringe 12. Hence, the pipe 9 prevents voltage noise from reaching the flow cell 6.

However, the method of grounding the sample liquid, described above, cannot be effectively used in a conventional ion concentration analyzer of the type, wherein the sample liquid is grounded via another ground at a point adjacent to another noise-generating source including a power supply source, nor can the method be used successfully in a conventional ion concentration analyzer of the type, wherein a plurality of cells is connected to the syringe by pipes. This is because multipoint grounds are provided and because current flows between these grounds when grounding is made between each of the flow cells and the syringe, thus causing it to detect an electric voltage including the noise. Moreover, the provision of a ground per se may expose an operator to a danger of an electric shock.

SUMMARY OF THE INVENTION

Accordingly, the object of the present invention is to provide an ion concentration analyzer, wherein the voltage noise generated in a sample liquid can be prevented influencing an ion selecting voltage, without necessity of grounding at all.

A further object of the invention is to provide an ion concentration analyzer, which is capable of safely avoiding a voltage noise.

To achieve the object, a metal member is located in a pipe connecting a flow cell to the syringe, hence in contact with the sample liquid flowing through the pipe, and is electrically connected to the piston rod of the syringe directly or by a conductive member.

According to the invention, one end of a conducting member is connected to a conductive line between an electrode for measuring a difference in electrical voltage in a sample liquid and a voltage noise generating source and the other end of the conducting member is electrically connected to a portion of the apparatus so as to interpose the voltage generating source there between, and to electrically insulate a portion between the connecting portions of the conducting member. Therefore, the voltage noise, if generated, is caused to pass through an electrical channel formed by the conducting member, thus prevented from reaching to the measuring electrode.

According to the invention, there is provided an ion concentration analyzer comprising a flow cell having an ion selecting electrode, and a syringe for introducing sample liquid into the flow cell, said syringe having a metal piston rod and a sliding block secured to the distal end of the piston rod and made of elastic insulating material so as to introduce sample liquid into the flow cell. The analyzer further comprises a metal member located in a pipe connecting the flow cell to the syringe, placed in contact with the sample liquid flowing through the pipe, and electrically connected to the piston rod directly or by a conductive member.

As has been described, the metal member is located in the pipe connecting the flow cell to the syringe, contacts the sample liquid flowing through the pipe, and is short-circuited to the metal piston rod. Therefore, the voltage noise generated while the syringe is being operated can be prevented from influencing the flow cell.

According to the invention there is also provided an ion concentration analyzer comprising an electrode for measuring a voltage of a sample liquid; a pipe for passing the sample liquid through the electrode; a mean for transfusing the sample liquid through the pipe; and a conductive member whose end portions are connected respectively to portions of the pipe different from each other in lengthwise of the pipe, said portions being located at the upstream of the electrode, thereby electrically insulating the interval between the end portions of the conducting member against the sample liquid.

In this case, the conducting member may be mounted on the outer wall of the conductive member, or may be mounted inside wall of the conductive member by covering the conductive member except the both ends thereof.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and together with the general description given above and the detailed description of the preferred embodiment given below, serve to explain the principles of the invention.

DETAILED DESCRIPTION OF THE PREFERRED EMBODIMENTS

Figure 1:
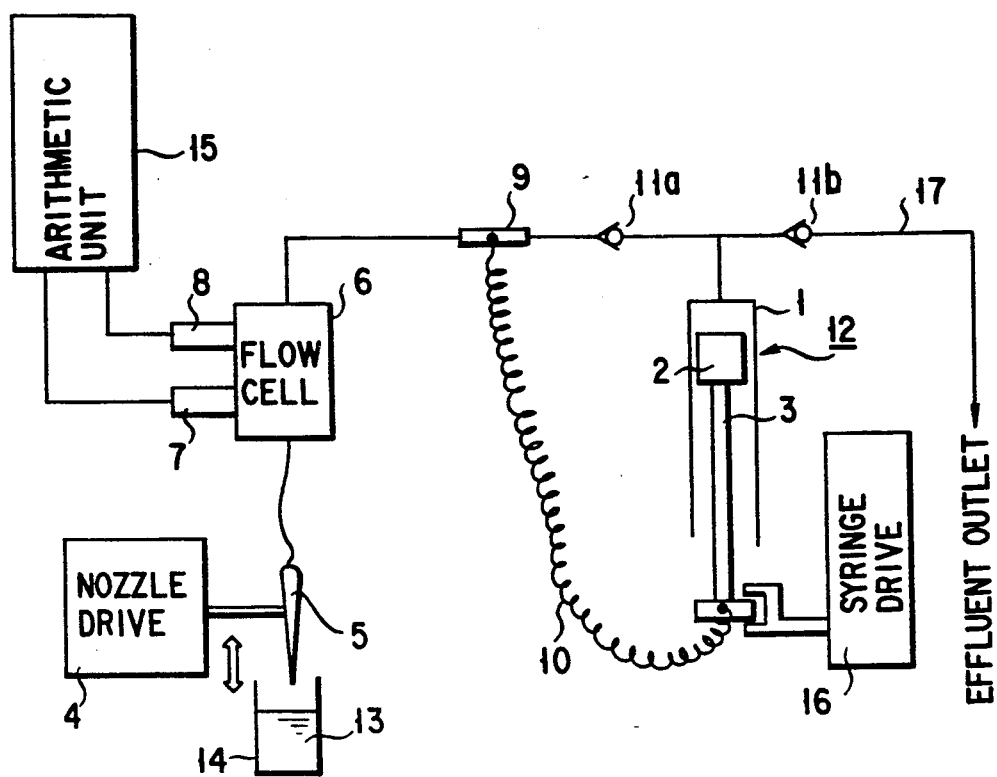
FIG. 1 is a schematic diagram showing an ion concentration analyzer according to the present invention.

FIG. 1 shows an ion concentration analyzer according to the invention. This analyzer is identical to the conventional one shown in FIG. 3, except for some respects. Therefore, the same components as those shown in FIG. 3 will be denoted at the same reference numerals and will now be described in detail.

As is shown in FIG. 1, analyzer comprises a flow cell 6, a sample nozzle 5, a nozzle drive mechanism 4, an ion selecting electrode 7, a reference electrode 8, a metal pipe 9, a conductor 10, check valves 11a and 11b, a syringe 12, an arithmetic unit 15, a syringe drive mechanism 16, and a liquid discharging pipe 17. The flow cell 6 has an opening, through which to feed and discharge sample liquid. The sample sucking nozzle 5 is connected to the opening of the flow cell 6. The nozzle drive mechanism 4 is designed to move the nozzle 5 up and down. The electrodes 7 and 8 are attached to the flow cell 6. The arithmetical unit 15 is designed to calculate the ion concentration of the sample liquid from the information supplied from the electrodes 7 and 8. The syringe 12 is connected to the opening of the flow cell 6 by the metal pipe 9 and a check valve 11a. The syringe 12 comprises a glass cylinder 1 and a piston 3 made of metal and slidably inserted in the cylinder 1. The syringe drive system 16 is designed to reciprocate the piston rod 3 in the glass cylinder 1. The check valve 11b is provided on the liquid discharging line 17, which connects to the syringe 12 to an outlet. Hence, the sample liquid can be discharged from the the syringe 12 through the line 17 and the outlet. The conductor 10 electrically connects the piston rod 3 of the syringe 12 to the metal pipe 9.

Figure 2:
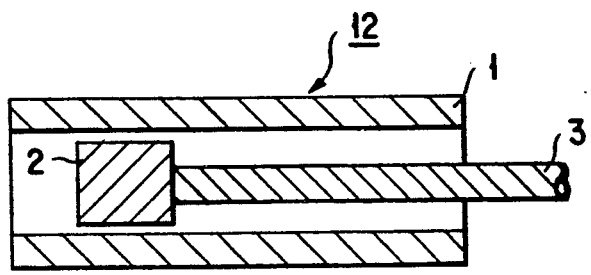
FIG. 2 is an enlarged, sectional view showing the syringe incorporated in the ion concentration analyzer according to the invention.

As is evident from FIG. 2, the metal piston rod 3 of the syringe 12 has, at its distal end, a sliding block 2 made of elastic insulator such as PTFE. The block 2 is slidably inserted in the glass cylinder 1.

Figure 3:
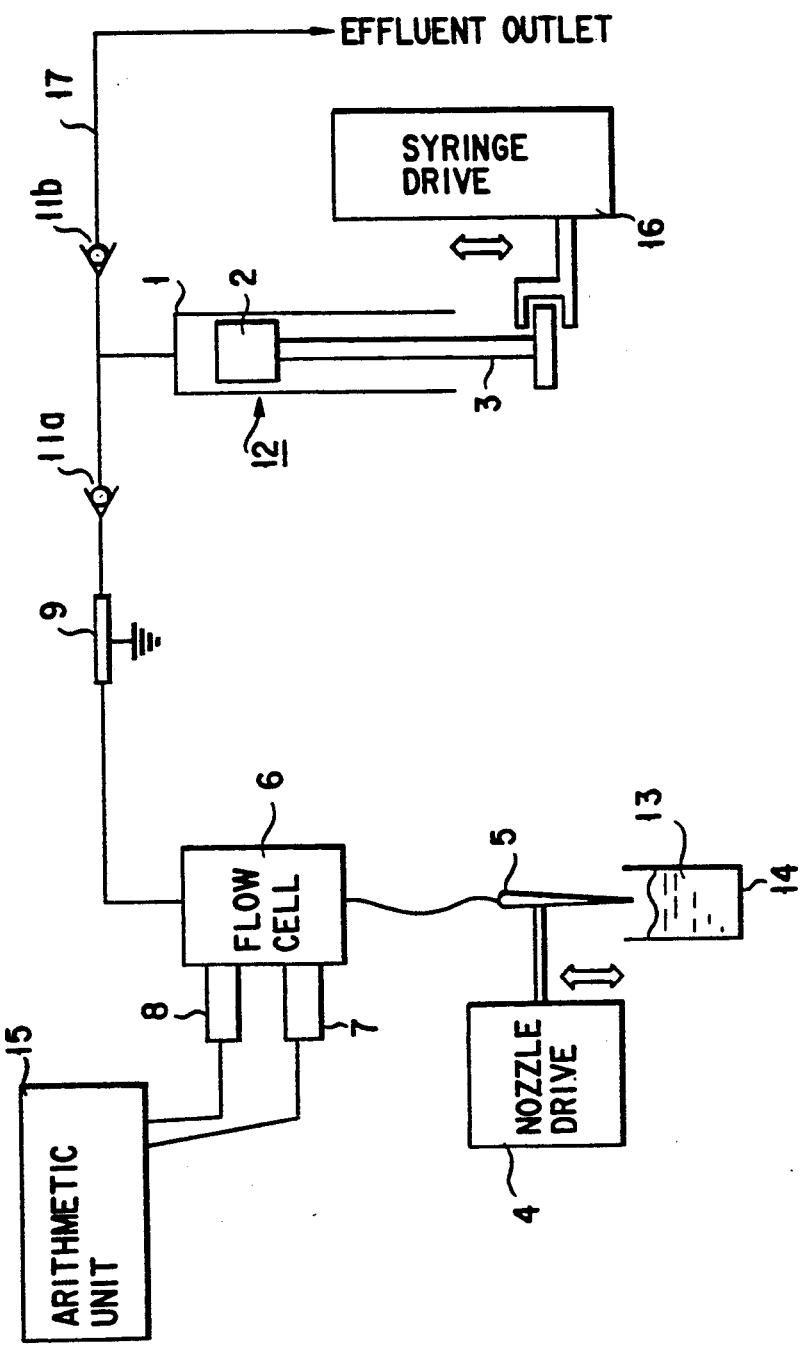
FIG. 3 is a schematic representation of an conventional ion concentration analyzer.

In the conventional ion concentration analyzer, the metal pipe 9 is grounded, as is shown in FIG. 3, to prevent voltage noise caused during the operation of the syringe 12 from influencing the flow cell 6. By contrast, in the ion concentration analyzer of the present invention, the piston rod 3 of the syringe 12 is connected to the metal pipe 9 by the conductor 10 and set at the same potential as the metal pipe 9, and the piston rod 3 and the metal pipe 9 are insulated from the ground.

It will now be explained how the ion concentration analyzer shown in FIG. 1 operates.

A sample container transfer system (not shown) transfers a container 14 containing sample liquid 13 to the ion concentration analyzer, and then places the container under the sample sucking nozzle 5. The nozzle drive system 4 lowers the nozzle 5 until the lower end of the nozzle 5 is put into the the sample liquid 13. Then the syringe drive system 16 drives the metal-made piston rod 3 in the cylinder 1 downwards (FIG. 1), in a sample sucking direction. As as a result, the sample liquid is introduced from the container 14 into the flow cell 6. Next, the syringe drive system 16 dries the piston rod 3 in the cylinder 1 upwards (FIG. 1), in a sample discharging direction. The sample liquid 13 is thereby discharged from the syringe 12 through the check valve 11b and the outlet. The syringe 12 can then supply the next sample liquid into the flow cell 6.

In the meantime, the sample liquid 13 is kept stationary in the flow cell 6. Therefore, the potential of the ion selective electrode 7 is gradually stabilized. When the potential of the electrode 7 becomes sufficiently stable, it is measured relative to that of the reference electrode 8. The arithmetic unit 15 converts the potential, thus measured, into an ion concentration value.

The sample liquid may leak during the wear of the sliding block 2 of the syringe 12 and contact the metal piston rod 3. If this happens, voltage noise is generated between the piston rod 3 and the sample liquid 13 in the syringe 12 while the liquid 13 is being introducing into, or discharged from, the syringe 12. The voltage noise, thus generated, is immediately discharged through the conductor 10 and the metal pipe 9. Hence, the voltage noise imposes no influence on the potential measurement of the ion selective electrode 7.

The metal piston rod 3, the conductor 10, and the metal pipe 9 constitutes a discharge path. This discharge path achieves the following advantages.

Figure 4:
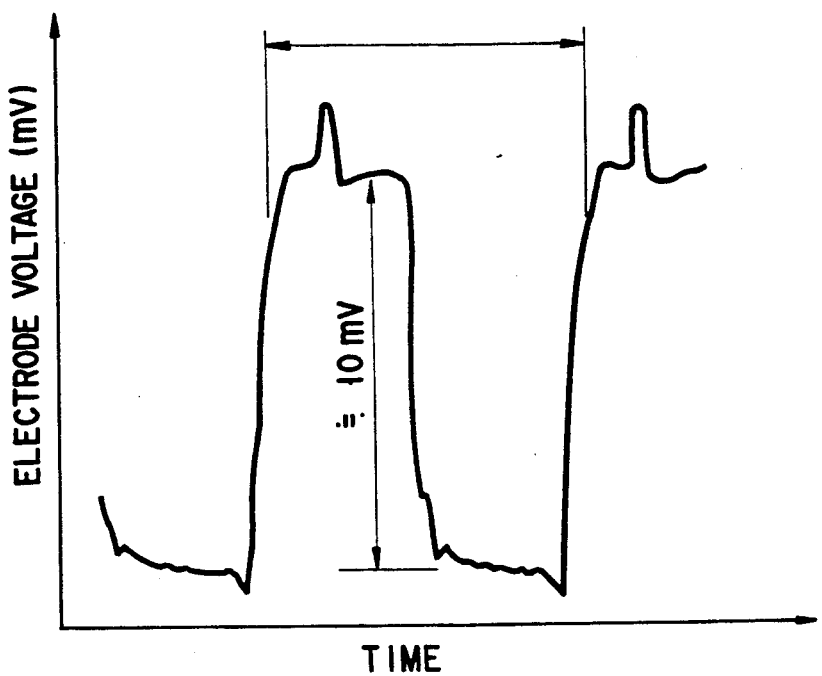
FIG. 4 is a graph illustrating how the electrode voltage changes when the discharge path is opened in the concentration analyzer shown in FIG. 1.
Figure 5:
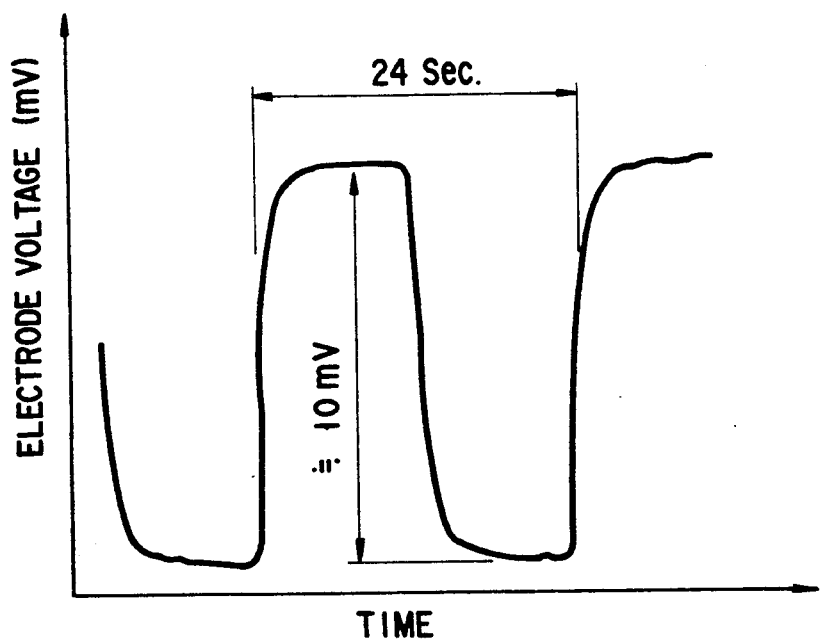
FIG. 5 is a graph showing how the electrode voltage changes when the discharge path is closed in the ion concentration analyzer shown in FIG. 1.

FIG. 4 is a graph illustrating how the potential of an Na ion electrode changes when the discharge path is opened in the ion concentration analyzer. More specifically, FIG. 4 shows the results of the experiment, wherein the potential of the ion electrode was measured while two solutions (100 mmol/l and 150 mmol/l) having different Na ion concentrations were alternately introduced into the flow cell 6. FIG. 5 shows how the potential of the Na ion electrode changes when the discharge path is closed.

As is evident form FIG. 4, the voltage noise changed abruptly when the discharge path was open. By contrast, as can be understood from FIG. 5, no such abrupt changes occurred when the discharge path was closed. Obviously, the voltage noise did not influence the flow cell 6 at all, thanks to the use of the discharge path.

As has been described, in the ion concentration analyzer of the invention, a metal member is located in the line connecting the syringe to the flow cell, contacts the sample liquid flowing though the line, and is short-circuited with the metal piston rod. This prevents the voltage noise generated during the operation of the syringe from adversely influencing the flow cell.

Further, as has been described, the discharge path, which is formed by the metal-made piston rod of the syringe, the conductor, and the metal member, is completely insulated from the other components. Therefore, the discharge path can be used not only in an ion concentration analyzer wherein the sample liquid is earthed not at the point between the flow cell and the syringe but at any other point, but also in an ion concentration analyzer wherein two or more flow cells are connected to the syringe via two or more lines.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. An ion concentration analyzer comprising a flow cell having an ion selecting electrode, and a syringe for introducing sample liquid into the flow cell, said syringe having a metal piston rod and a sliding block secured to the distal end of the piston rod and made of elastic insulating material so as to introduce sample liquid into the flow cell, said analyzer further comprising:

a metal member located in a pipe connecting the flow cell to the syringe, placed in contact with the sample liquid flowing through the pipe, and electrically connected to the piston rod directly or by a conductive member.

2. An ion concentration analyzer according to claim 1, wherein an arithmetic unit is connected to the flow cell through an ion selecting electrode and a reference electrode attached to the flow cell.

3. An ion concentration analyzer according to claim 1, wherein said metal member is of tubular form, and mounted to communicate with said pipe.

4. An ion concentration analyzer comprising an electrode for measuring a voltage of a sample liquid; a pipe for passing the sample liquid through the electrode; a means for transfusing the sample liquid through the pipe; and a conductive member whose end portions are connected respectively to portions of the pipe different from each other in lengthwise of the pipe, said portions being located at the upstream of the electrode, thereby electrically insulating the interval between the end portions of the conducting member against the sample liquid.

* * * * *